(12) United States Patent
De Clerck

(10) Patent No.: US 12,708,550 B2
(45) Date of Patent: Aug. 18, 2026

(54) JAW DISPLACEMENT SYSTEM AND METHOD FOR MANUFACTURING SUCH A SYSTEM FOR THE TREATMENT OF SLEEP APNOEA AND/OR SNORING

(71) Applicant: TITA-LINK B.V., Brussels (BE)

(72) Inventor: Hugo De Clerck, Tervuren (BE)

(73) Assignee: TITA-LINK B.V., Brussels (BE)

( * ) Notice: Subject to any disclaimer, the term of this patent is extended or adjusted under 35 U.S.C. 154(b) by 0 days.

(21) Appl. No.: 17/059,577

(22) PCT Filed: May 31, 2019

(86) PCT No.: PCT/IB2019/054558
§ 371 (c)(1),
(2) Date: Nov. 30, 2020

(87) PCT Pub. No.: WO2019/229724
PCT Pub. Date: Dec. 5, 2019

(65) Prior Publication Data

US 2021/0205119 A1 Jul. 8, 2021

(30) Foreign Application Priority Data

May 30, 2018 (BE) .................................. 2018/0069

(51) Int. Cl.
*A61F 5/56* (2006.01)

(52) U.S. Cl.
CPC .................................... *A61F 5/566* (2013.01)

(58) Field of Classification Search
CPC .... A61F 5/56; A61F 5/566; A61F 5/58; A61F 5/0006; A61C 7/36; A61C 7/10; A61C 7/00; A61C 8/00–0098
USPC ........................... 128/848; 433/5, 19, 24, 21
See application file for complete search history.

(56) References Cited

U.S. PATENT DOCUMENTS

| | | | | |
|---|---|---|---|---|
| 11,376,025 B2 * | 7/2022 | De Clerck | A61C 1/084 | |
| 2006/0172251 A1 | 8/2006 | Voudouris | | |
| 2007/0190477 A1 * | 8/2007 | Sheikh | A61C 7/36 | 433/19 |
| 2010/0139666 A1 * | 6/2010 | Bonnaure | A61F 5/566 | 128/848 |
| 2014/0255866 A1 * | 9/2014 | Faust | A61C 7/20 | 433/19 |
| 2017/0172785 A1 | 6/2017 | Rogers | | |
| 2019/0255778 A1 * | 8/2019 | Lucas | G05B 19/4099 | |

FOREIGN PATENT DOCUMENTS

| | | |
|---|---|---|
| EP | 1073379 A1 | 2/2001 |
| FR | 3011460 A1 | 4/2015 |
| WO | 2010037195 A1 | 4/2010 |
| WO | 2010087824 A1 | 8/2010 |
| WO | 2016100577 A1 | 6/2016 |
| WO | 2017095971 A1 | 6/2017 |
| WO | 2017106896 A1 | 6/2017 |

* cited by examiner

*Primary Examiner* — Alireza Nia
*Assistant Examiner* — Robin Han
(74) *Attorney, Agent, or Firm* — FisherBroyles, LLP; Roger L. Browdy; Ronni S. Jillions

(57) ABSTRACT

A jaw displacement system is provided for the treatment of sleep apnoea and/or snoring and a method for manufacturing this system. Bone anchors are provided on the upper and lower jaw of a patient, between which a detachable jaw displacer is mounted.

25 Claims, 3 Drawing Sheets

27
11
3
4
2
6
10
26

10
15
13
17
16
6
5
1
11
12
3
2
6

8
9
10
7
12
3
1,2

6
10
7

27
11
3
4
2
6
15
10
13
17

16
10
6
14
1
5
11
15
18
24
21
23
17
20
16
18
14
19
22
25

18
23
20
19
16
18
22
21
17
25
14

14
18
17
16
25
19
23
21b
20
21
21a
24
15
22

JAW DISPLACEMENT SYSTEM AND METHOD FOR MANUFACTURING SUCH A SYSTEM FOR THE TREATMENT OF SLEEP APNOEA AND/OR SNORING

The invention concerns a jaw displacement system for the treatment of sleep apnoea and/or snoring. This system includes a first and a second bone anchor, where each bone anchor has a fixation plate that is provided to attach the bone anchor to the bone of an upper or lower jaw. The fixation plate is connected to a connecting element that leads to a mounting device. When the bone anchor is attached to the bone of the upper or lower jaw, the connecting element should stretch through the gum so that the mounting device is located in the oral cavity.

This jaw displacement system also includes a jaw displacer with a rod and a rod guide. The rod has a first end of the jaw displacer, while the rod guide contains a second end of the jaw displacer opposite to the latter. The rod can be moved according to the longitudinal direction of the rod guide and can be detached in relation to the latter.

The jaw displacement system further has coupling means which allow each of said ends of the jaw displacer to be detachably connected to the mounting device of the first or second bone anchor, respectively.

One of the possible treatments for sleep apnoea is to move a patient's lower jaw slightly forward with respect to the upper jaw while sleeping. According to the state of the art, this is done, for example, with the aid of removable braces that rest on the teeth of the upper and lower jaw. Such systems are described in documents US 2017/172785, WO 2010/087824, WO 2016/100577, WO 2017/095971 or WO 2017/106896. However, these systems appear to be disadvantageous in that they change the position of the teeth in the jaw after only a short period of time due to the continuous pressure exerted on them while carrying the braces.

Document WO 2010/037195 attempts to remedy this disadvantage by providing an implant in the upper and lower jaw with a detachable compression spring between these implants. However, this system does not appear to provide satisfactory results. It is also difficult and inconvenient for a patient to loosen and remove the compression spring from the mouth and replace it. In addition, the use of the system from WO 2010/037195 can result in a patient sleeping with open mouth, which increases the intensity of snoring.

Document US 2006/172251 describes a similar jaw displacement system that is used in orthodontic applications, but contains a compression spring that is screwed to implants and therefore is not suitable for easy assembly or removal by a patient.

The invention aims to remedy these disadvantages by proposing a jaw displacement system for the treatment of sleep apnoea and/or snoring with a jaw displacer that can be easily removed from or fitted back into his/her mouth by a patient. The use of the invention has virtually no effect on the position of the teeth and greatly reduces the incidence of sleep apnoea and/or snoring.

Thus, the invention concerns a sleep apnoea prevention system in which a jaw displacer can be easily and quickly mounted in the mouth by the patient when going to sleep, while this jaw displacer can be easily removed from the mouth during the day. The system according to the invention hereby allows the mouth to be fully opened without any parts of the jaw displacer accidentally coming loose and possibly being swallowed, for example, during sleep.

To this aim, said connecting means include a hook and eye, with the hook attached in a detachable manner to the eye.

Practically, said rod guide contains a spring element, so that the rod guide can be deformed longitudinally between a compressed state and an extended state.

Said spring element is formed, for example, by a cylindrical coil spring.

According to a preferred embodiment of the system according to the invention, said rod guide contains a tube with a first tube end and a second tube end, whereby said coupling means, preferably said eye, are provided at the first tube end, while the spring element, when not compressed, extends along the tube to at least the second tube end, the spring element being required to interact with said rod, when the jaw displacement system is mounted in the oral cavity, in order to exert a compressive force on said rod in the longitudinal direction of the rod guide.

According to an interesting embodiment of the jaw displacement system according to the invention, said tube is a telescopic tube with parts which can freely move in relation to one another, which parts can be moved between a retracted position and an extended position, in which said spring element exerts a compressive force on these parts according to said longitudinal direction in order to bring them into the extended position.

Advantageously, opposite ends of said spring element are connected to said first and second tube ends respectively.

According to a special embodiment, said spring element is, preferably, coaxial with said tube, while said tube extends at least partially into said spring element.

The invention also concerns a method of manufacturing a jaw displacement system for the treatment of sleep apnoea and/or snoring by moving the lower jaw forward, in a ventral direction, in relation to the upper jaw.

According to this method, a first and a second bone anchor are provided, with each bone anchor containing a fixation plate that allows the bone anchor to be attached to the bone of an upper or lower jaw. The fixation plate is connected to a connecting element that leads to a mounting device. The connecting element should stretch through gums when the bone anchor is attached to said bone so that the mounting device is in the oral cavity.

When manufacturing the jaw displacement system, a jaw displacer with a first and a second end is used as well, in which the jaw displacer contains a rod with said first end and a rod guide provided with said second end. The rod is mounted in a movable manner in the longitudinal direction of the rod guide and in a detachable manner in relation to the latter.

The rod guide is equipped with a spring element so that the rod guide can be deformed in its longitudinal direction between a compressed state and an extended state.

Further, coupling means are provided which allow to connect each of said ends of the jaw displacer in a detachable manner to the mounting device of the first or second bone anchor, respectively. The coupling means include, for example, a hook and eye, whereby the hook can be attached to the eye in a detachable manner.

This method is characterised in that the position of the mounting device of the first and second bone anchor respectively in relation to the associated fixation plate is selected such that, taking into account the dimensions and geometry of the lower and upper jaws, a connecting line is established between the coupling means of said ends of the jaw displacer, in particular a connecting line between the support points of the respective coupling means, extending on the side of the lower jaw below the rotation point of the lower jaw in relation to the upper jaw when both bone anchors are attached to the respective jaws, and the jaws are placed against each other in a closed position or, more generally, the mouth is closed. These support points are, for example, the support points between the hook and the eye of the respective coupling means when the jaw displacer is mounted on the bone anchors and the mouth is closed.

According to a particular embodiment of the method according to the invention, the length of the rod, increased by the length of the rod guide in said extended condition, is selected greater than the distance between said mounting elements of the first and second bone anchors if they were attached to the respective jaws and the jaws are in a wide open position, while the length of the rod, increased by the length of the rod guide when it is in a compressed condition, is smaller than that distance.

According to a preferred embodiment of the method according to the invention, a model of the upper and lower jaw is generated, whereby the first bone anchor is designed with a fixation plate that can be fitted to a selected part of the upper jaw, and said second bone anchor is designed with a fixation plate that can be fitted to a selected part of the lower jaw.

Other particularities and advantages of the invention will become clear from the following description of some specific embodiments of the jaw displacement system and its manufacturing method according to the invention. This description is given as an example only and does not limit the scope of the claimed protection; the reference figures used below refer to the accompanying drawings.

In the different figures, the same reference figures refer to the same or similar elements.

The invention in general concerns a jaw displacement system which is particularly interesting for treating sleep apnoea. With the aid of this system, a patient's lower jaw is moved slightly forward in relation to the upper jaw while sleeping, in such a way that sleep apnoea is eliminated or at least the frequency of its occurrence is significantly reduced. In addition, this system also appears to ensure that snoring during sleep is at least reduced.

Existing systems for treating sleep apnoea are quite complex or cumbersome to apply. In addition, many systems that apply pressure to the teeth cause undesirable displacement of the teeth after a short period of time.

The system according to the invention not only allows an effective treatment of sleep apnoea without affecting the teeth, but is also very user-friendly in that it can be easily placed in the mouth by a patient before going to bed and can be easily removed after waking up. In addition, the risk that parts of the jaw displacement system unintentionally come off while sleeping is virtually non-existent. Indeed, if parts of the jaw displacement system were to accidentally come off, there is a risk that they would be swallowed or end up in the respiratory tract.

Figures 1, 3, 10:
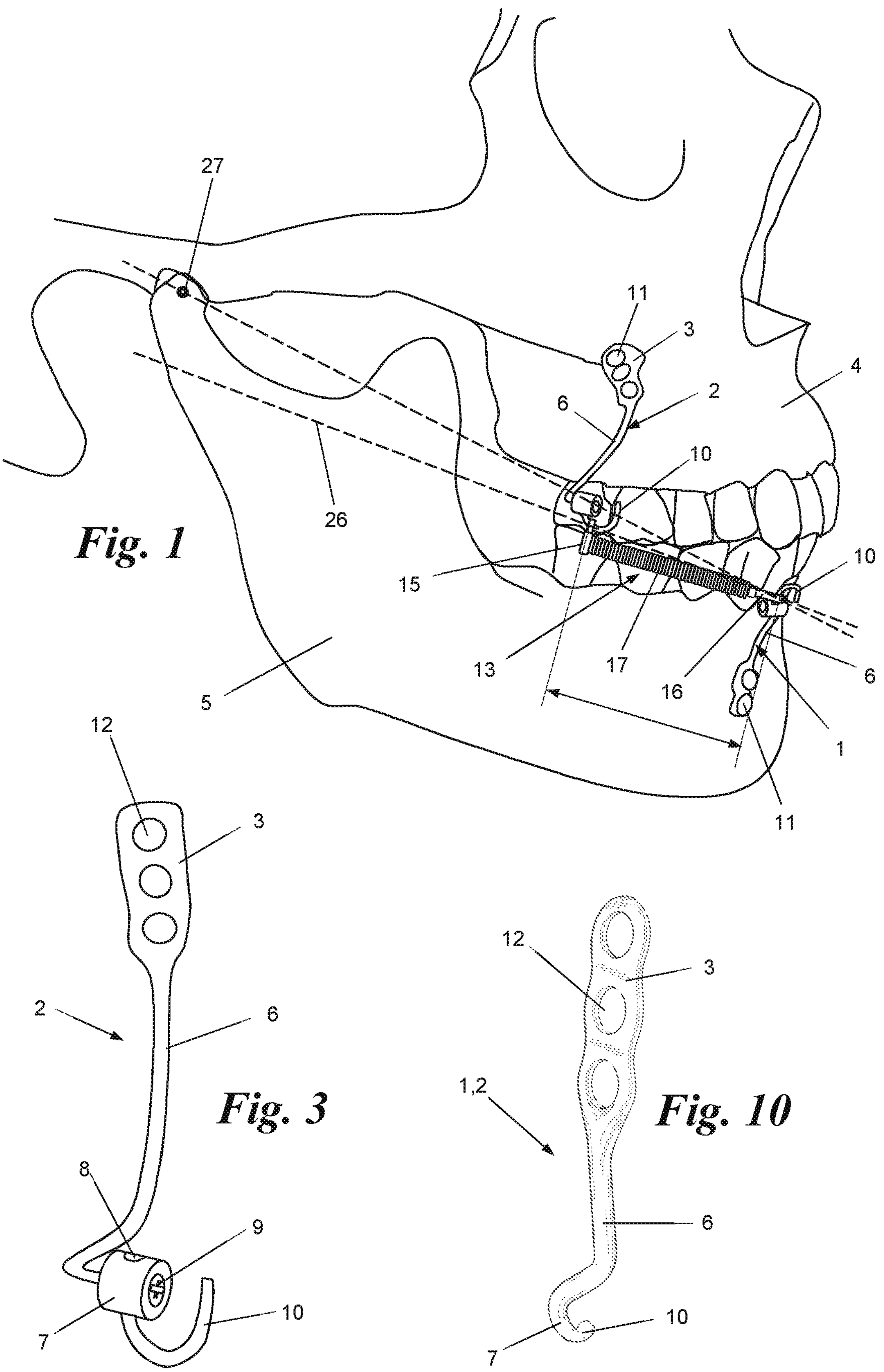
FIG. 1 is a schematic side view of a skull equipped with a jaw displacement system according to the invention, when the jaws are in a closed position.
FIG. 3 is a schematic representation of a bone anchor of the jaw displacement system according to the invention.
FIG. 10 is a schematic representation of a bone anchor of the jaw displacement system according to another embodiment of the invention.
Figures 2, 8, 9:
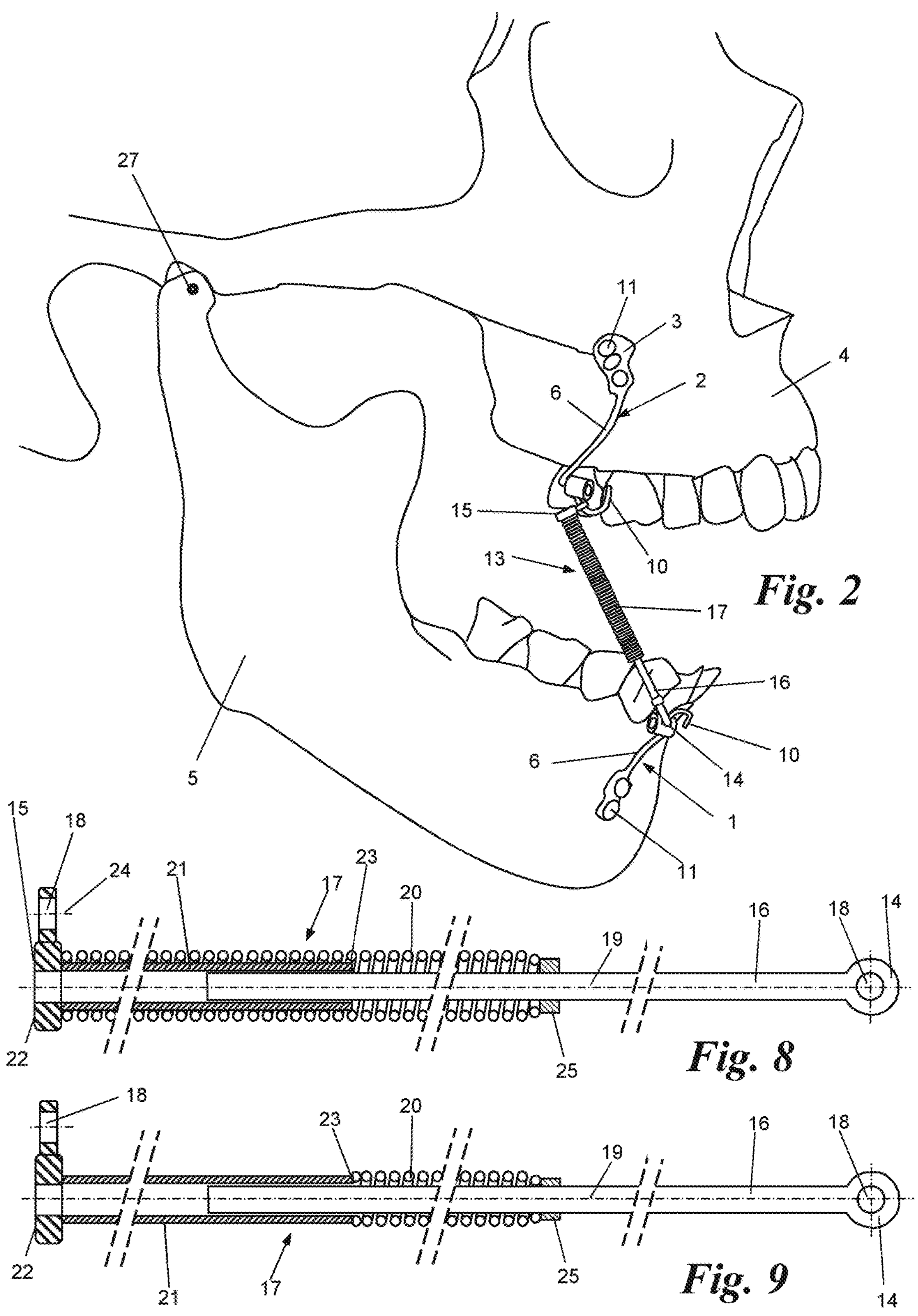
FIG. 2 is a schematic side view of the skull with the jaw displacement system from FIG. 1 when the jaws are in an open position.
FIG. 8 is a schematic longitudinal section of a jaw displacer according to an alternative embodiment of the invention.
FIG. 9 is a schematic longitudinal section of a jaw displacer according to a variant embodiment of the invention.

FIGS. 1 and 2 schematically show a jaw displacement system according to the invention when it is attached to a patient's jaws.

This jaw displacement system contains a first bone anchor 1 and a second bone anchor 2. Each bone anchor is equipped with a fixation plate 3 that allows the bone anchor 1 or 2 to be attached to the bone of an upper jaw 4 or of a lower jaw 5 with screws 11 that must extend through recesses 12 in the fixation plate 3. The fixation plate 3 connects to a connecting element 6 that leads to a mounting device 7. FIG. 3 shows a schematic bone anchor 2.

The connecting element 6 must pass through gums when the bone anchor 1 or 2 is attached to said bone so that the mounting device 7 extends in the oral cavity. The connecting element 6 is preferably formed here by a curved, relatively stiff rod with a circular cross-section.

The mounting device 7 is formed by a cylindrical organ whose axis extends in line with the far end of the connection element 6 while a bore 8 is provided across this axis through the mounting device 7. Furthermore, according to the axial direction of the mounting device 7, a fixation screw 9 stretches out, which opens in the above-mentioned bore 8. Thus, this fixing screw 9 allows a hook 10, one end of which extends through the hole 8, to be attached to the mounting device 7.

Furthermore, the jaw displacement system includes a jaw displacer 13 with a first end 14 and a second end. This jaw displacer 13 contains a rod 16 with this first end 14 and a rod guide 17 provided with the second end 15. The rod 16 can be moved according to the longitudinal direction of the rod guide 17 and is mounted in a detachable manner in relation to the latter. Preferably, the rod 16 is formed by a straight rod with a circular cross-section.

In order to attach the jaw displacer 13 with its first and second ends 14 and 15 to the mounting devices 7 of the bone anchors 2 and 3, coupling means are provided. In particular, these coupling means allow each of said ends 14 and 15 of the jaw displacer 13 to be connected to the mounting device 7 of the first or second bone anchor 1 and 2 respectively in a detachable manner.

According to a preferred embodiment of the invention, each of these coupling means contains a hook 10 and an eye 18. The hook 10 can hereby hook in the eye 18 in a detachable manner in order to attach them to each other.

FIGS. 4 to 7 show the jaw displacer in more detail. In the proposed embodiment of the jaw displacer 13, each of the ends 14 and 15 is provided with an eye 18 of the coupling means. In addition, a hook 10 is attached to the mounting device 7 of each of the bone anchors 1 and 2, in the bore 8, to allow the jaw displacer 13 to be attached with the eyes 18 to the hooks 10 of the bone anchors in a detachable manner as will be described below.

Said rod guide 17 has a longitudinal axis 19 according to which it can be deformed between a compressed state and an extended state. For this purpose, the rod guide 17 contains a spring element 20 which is formed by a cylindrical coil spring.

Furthermore, the rod guide contains a tube 21 with a first tube end 22 and a second tube end 23. An eye 18 of said coupling means is fixed to this first tube end 22. This eye 18 is thus fixed to the rod guide 17 and has a central axis 24 that is almost parallel to the longitudinal direction of the rod guide 17. The central axis 24 of this eye 18 consequently extends, in this embodiment, parallel to the longitudinal axis 19.

Figures 4, 5, 6, 7:
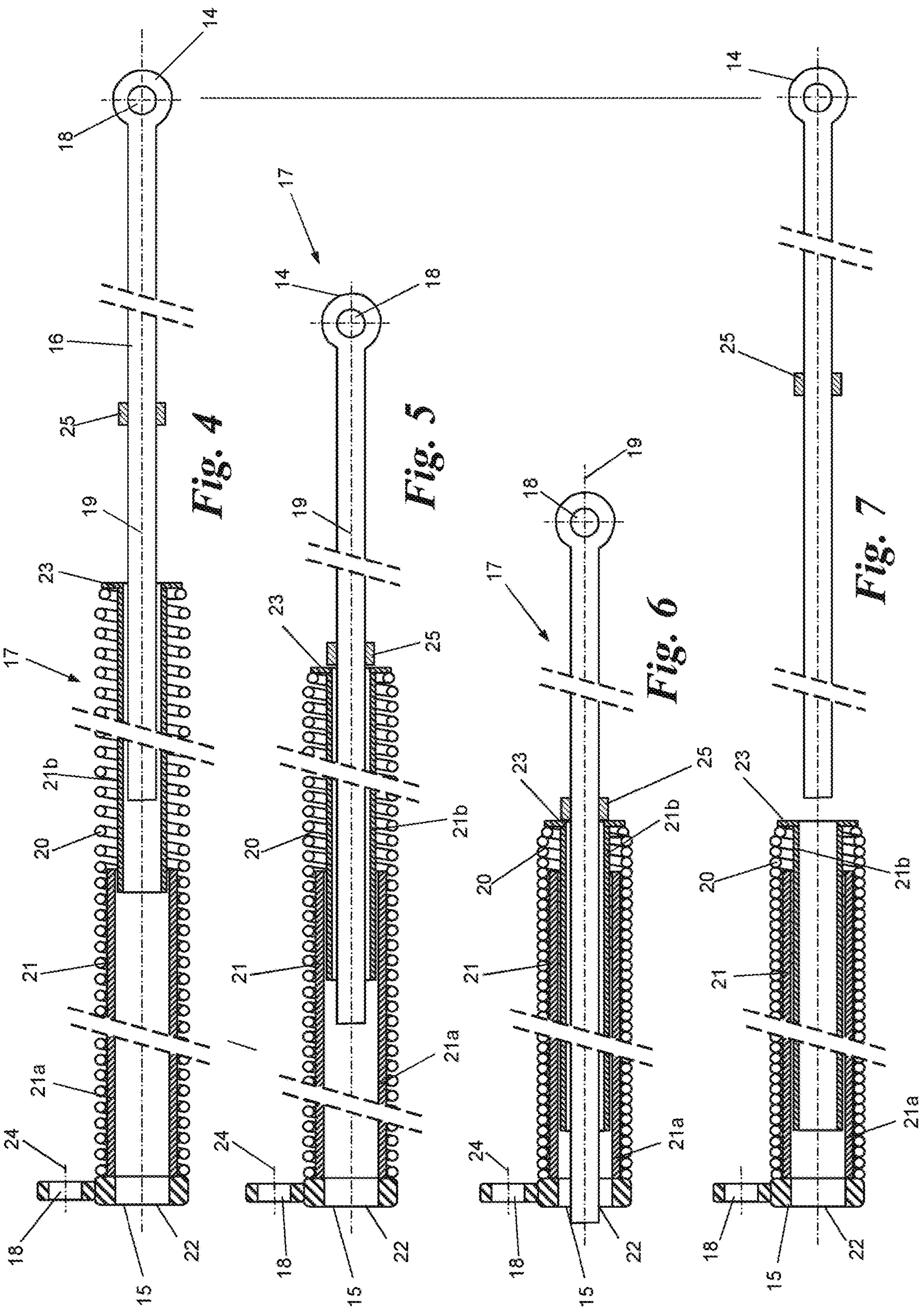
FIG. 4 is a schematic longitudinal section of a jaw displacer according to an interesting embodiment of the invention, with a rod guide in an extended state.
FIG. 5 is a schematic longitudinal section of the jaw displacer in FIG. 4, where the rod guide is in an intermediate position between a compressed and an extended state.
FIG. 6 is a schematic longitudinal section of the jaw displacer from FIGS. 4 and 5, where the rod guide is in the compressed state.
FIG. 7 is a schematic longitudinal section of the jaw displacer from FIGS. 4 to 6, where the rod guide is in the compressed state and the rod is removed from the rod guide.

The spring element 20, formed by the aforementioned cylindrical spring, extends along the tube 21 between its two ends 22 and 23. In the embodiment of the jaw displacer 13 shown in FIGS. 4 to 7, said tube 21 is formed by a telescopic tube with parts 21*a* and 21*b* that can freely move in relation to each other. These parts 21*a* and 21*b* are movable between a retracted position, as shown in FIGS. 6 and 7, and an extended position, as shown in FIG. 4.

The spring element 20 exerts a compressive force on these parts 21*a* and 21*b* according to the longitudinal direction mentioned above, so that they are moved to the extended position when no counter-pressure is exerted. In particular, the spring element 20 exerts a compressive force between the ends 22 and 23 of the telescopic tube 21 and, preferably, it is firmly connected to these ends 22 and 23. The tube 21 extends into the spring element 20, and the tube 21 and the spring element 20 are coaxial.

In order to mount the jaw displacer 13 in the oral cavity on bone anchors 1 and 2 provided there, the eye 18, located at the end of rod 16, is attached to the hook 10 which is fixed to the first bone anchor 1. The rod guide 17 is attached with the corresponding eye 18 to the hook of the second bone anchor 2. The jaws 4 and 5 are then moved into an open position, as shown in FIG. 2, and a compression force is manually applied to the free end 23 of the rod guide 17 in its longitudinal direction so that it deforms into the compressed state as shown in FIG. 7. In order to insert the rod 16 into the rod guide 17, its free end, opposite the eye 18, is placed opposite the end 23, as shown in FIG. 7. Preferably, care should be taken to ensure that the rod guide 17 and the rod 16 extend coaxially, at least approximately. Next, the spring element 20 is relaxed so that the tube 21 slides over the rod 16.

In manufacturing the jaw displacement system, it has been ensured that the length of the rod 16, increased by the length of the rod guide 17 in said extended condition, is greater than the distance between the hooks 10 which are fixed to the mounting elements 7 of the bone anchors 1 and 2 when they are attached to the respective jaws 4 and 5 and these jaws 4 and 5 are in a wide open position, while the length of the rod 16, increased by the length of the rod guide 17 when it is compressed, is smaller than said distance.

This ensures that, when the jaw displacer is mounted in the oral cavity, the rod 16 can only be removed from the rod guide 17 if the rod guide is moved manually into the compressed state.

When the jaw displacer 13 is mounted in the oral cavity on the bone anchors 1 and 2, as shown in FIGS. 1 and 2, as the jaws are moved into a closed position, the rod 16 will be gradually pushed further into the tube 21 of the rod guide 17.

The rod 16 is equipped with a stop element 25 which is formed, for example, by a ring that is clamped around the rod 16 in a chosen position, as is shown in the figures. If necessary, this stop element can be formed by a stop tube with a length chosen as a function of the geometry and the dimensions of the jaws 4 and 5. This stop tube is then pushed over the rod 16 until it rests against a thickening in the rod formed by, for example, said eye 18.

When the jaws 4 and 5 are closed, the rod 16 moves in the rod guide 17 until the stop element 25 comes into contact with the spring element 20 or the end 23 of said tube 21, as shown in FIG. 5. When the jaws 4 and 5 are closed further, a force of pressure is applied by the spring element 20, so that a force of pressure is applied in a ventral direction to the lower jaw 5 via the bone anchors 1 and 2. Depending on the compression force of the spring, the lower jaw 5 will thus be moved in the ventral direction with respect to the upper jaw 4.

When the jaws 4 and 5 are closed further, the spring element 20 is almost completely compressed as shown in FIG. 6, and the jaw displacer 13 thus forms an almost completely rigid element that ensures that the lower jaw 5 is moved in the ventral direction in relation to the upper jaw 4, which ensures that the sleep apnoea symptoms decrease or disappear when sleeping.

It should be noted that in certain cases, it is not required for the spring element 20 to be fully compressed when the jaws are in the closed position. For example, it may be sufficient to select the stiffness of the spring element 20 such that the lower jaw 5 will already be sufficiently displaced in relation to the upper jaw 4 in the event of a partial compression of the spring element 20.

Furthermore, the gradual compression of the spring element 20 ensures that the deformation of the jaw displacer 13 into the compressed state is slightly dampened so that no sudden loads affect the jaws 4 and 5 or components of the jaw displacement system.

When manufacturing the jaw displacement system, the position of the mounting device 7 of the first bone anchor 1 and of the second bone anchor 2 respectively in relation to the associated fixation plate 3 is selected such that, if both bone anchors 1 and 2 were attached to the respective jaws 4 and 5, a connecting line between the coupling means of the ends 14 and 15 of the jaw displacer 13 would extend to the side of the lower jaw 5 below the rotation point 27 of the lower jaw 5 in relation to the upper jaw 4.

The abovementioned connecting line 26 connects, in particular, the support points between the hook 10 and the eye 18 of each of the respective coupling means when the jaws 4 and 5 are in the closed position or, i.e. when the mouth is closed. This prevents the spring element 20 applying a force that would move the jaws from the closed position into the open position.

This connecting line 26 can also be formed with sufficient accuracy, approximately, by the longitudinal axis 19 of the jaw displacer 13 when the jaws are in the closed position.

Preferably, the jaw displacement system is manufactured on the basis of a physical or digital model of the upper and lower jaw. Based on such a model thus generated, the first bone anchor 1 shall be designed with a fixation plate 3 that can be fitted to a selected portion of the upper jaw 4, and the second bone anchor 2 shall be designed such that its fixation plate 3 can be fitted to a selected portion of the lower jaw 5. On the basis of this model, also the length of the rod 16 or of the rod guide 17 can be selected as a function of the geometric shape and dimensions of the jaws 4 and 5.

On the mounting device 7 of the bone anchors 1 and 2, a U-shaped hook 10 of the coupling means is preferably provided such that, when the respective bone anchor 1 or 2 is attached to the jaw 4 or 5, this hook 10 will extend parallel to the dental arch of the jaw 4 or 5 or, in particular, it will extend in a plane which is tangential to this dental arch.

Such a choice for the orientation of the hooks 10 ensures that the jaw displacer can easily be mounted in and out of the oral cavity and that the coupling means do not unintentionally come loose.

Preferably, the hook 10 should be provided on the mounting device 7 in such a way that its open side extends to the side of the jaw 4 or 5 concerned, while the closed side of the hook extends to the occlusal plane.

In addition, FIGS. 8 and 9 show alternative embodiments of the jaw displacer in a position similar to that of the jaw displacer in FIG. 5.

It is also possible for the hook 10 of the coupling means to be integrated with the mounting device 7, so that the hook 10 forms a whole with the bone anchor 1 or 2.

Of course, the coupling means in the jaw displacement system or the method according to the invention are not limited to a hook 10 working together with an eye 18, but alternative means of coupling can be provided by the person skilled in the art. For example, it is possible for these coupling means to contain two hooks which are connected in a detachable manner. For example, the coupling means may contain two corresponding parts which click together according to a male-female principle.

In certain cases, it may be interesting to give the jaw displacer a slightly curved shape in order to make it follow almost the same curve as the dental arch. In that case it is avoided, for example, that the jaw displacer makes disruptive contact with the teeth when opening or closing the mouth. In this way, the rod 16 and, if necessary, also the rod guide 17, are curved.

The invention is of course not limited to the embodiments of the jaw displacement system or of the method described above and shown in the accompanying figures. Within the scope of the invention, several alternatives can be considered.

The invention claimed is:

1. A method for manufacturing a jaw displacement system for treatment of sleep apnoea and/or snoring by moving a lower jaw forward, in a ventral direction, in relation to an upper jaw, comprising:

providing a first and a second bone anchor, in which each bone anchor contains a fixation plate that allows the bone anchor to be attached to a bone of the upper or lower jaw, wherein this fixation plate is connected to a first rod that leads to a mount and wherein the first rod must stretch through gums when the bone anchor is attached to said bone so that the mount is located in the oral cavity, wherein said first bone anchor is designed with said fixation plate that is intended to be fixed to a selected part of the upper jaw and said second bone anchor is designed with said fixation plate that is intended to be fixed to a selected part of the lower jaw anterior to the first bone anchor, providing a jaw displacer having a first end and a second end, and comprising a second rod disposed at said first end and a rod guide disposed at said second end, wherein the second rod is movable in a longitudinal direction of the rod guide and is detachable in relation to the rod guide, providing said rod guide with a spring so that the rod guide can be deformed in the longitudinal direction between a compressed state and an extended state, providing couplers which allow each of said ends of the jaw displacer to be connected in a detachable manner to the mount of the first bone anchor or the second bone anchor respectively, selecting a position of the mount of the first bone anchor and of the second bone anchor respectively in relation to the corresponding fixation plate such that, if both bone anchors were attached to the respective jaws, the mount of the second bone anchor is positioned anterior and inferior to the mount of the first bone anchor and a connecting line would be established between the couplers of said ends of the jaw displacer, said connecting line extending on a side of the lower jaw inferior to a rotation point of the lower jaw in relation to the upper jaw when the jaws are in a closed position, and wherein the spring cooperates with said second rod, when the jaw displacement system is mounted in the oral cavity, to exert a pushing force on the second rod in the longitudinal direction of the rod guide so that the lower jaw is moved forward in an anterior direction in relation to the upper jaw.

2. The method according to claim 1, wherein said couplers comprise a hook and eye, the hook of which can be fixed to the eye in a detachable manner.

3. The method according to claim 2, wherein the eyes of said couplers are attached to the ends of the jaw displacer in such a way that the eyes have a central axis which is parallel to a longitudinal axis of the jaw displacer.

4. The method according to claim 3, wherein one of said eyes is provided at said second end of the jaw displacer in such a way that a central axis thereof is parallel to a longitudinal axis of the rod guide.

5. The method according to claim 2, wherein the eyes of said couplers are provided at the ends of the jaw displacer in such a way that the eyes have a central axis transverse to a longitudinal axis of the jaw displacer.

6. The method according to claim 5, wherein one of said eyes is provided at said first end of the jaw displacer in such a way that a central axis thereof is transverse to a longitudinal direction of the second rod, the central axis intersecting the longitudinal axis of the jaw displacer.

7. The method according to claim 2, wherein said connecting line between the couplers of said ends of the jaw displacer connects support points between the hook and the eye of the coupler, respectively, and extends on the side of the lower jaw below the rotation point of the lower jaw in relation to the upper jaw when the jaws are in the closed position.

8. The method according to claim 1, where the lower and upper jaw, respectively, present a dental arch and where a U-shaped hook of each coupler is provided on the mount of said bone anchors in such a way that, when the first and second bone anchors is attached to the lower and upper jaw, respectively, the U-shaped hook will extend parallel to the dental arch of the lower and upper jaw, respectively or, in particular, in a plane which is tangential to the dental arch.

9. The method according to claim 8, where said upper and lower jaw define an occlusal plane and said hook is provided on the mount in such a way that an open side of the hook extends to a side of a concerned jaw, while a closed side of the hook extends to the occlusal plane.

10. The method according to claim 1, in which said rod guide is made hollow with an open end opposite the second end, in order to allow the second rod to be moved and guided in the rod guide according to its longitudinal direction.

11. The method according to claim 1, where a distance is present between the mount of the first and second bone anchors when attached to the lower jaw and upper jaw, respectively, and the lower jaw and the upper jaw are in a wide open position, where said second rod has a length and said rod guide has a length, wherein the length of the second rod plus the length of the rod guide in said extended state is selected greater than said distance, whereas the length of the second rod increased by the length of the rod guide when it is compressed, is smaller than said distance.

12. The method according to claim 1, where a ring or stop tube is fitted to said second rod, wherein the ring or stop tube works together with the rod guide in order to exert a pushing force between the mount of the first bone anchor and the mount of the second bone anchor when said bone anchors are attached to the lower and upper jaw, respectively.

13. The method according to claim 1, wherein a model of the upper jaw and of the lower jaw is generated, wherein said first bone anchor is designed with said fixation plate that can be fitted to a selected part of the upper jaw and said second bone anchor is designed with said fixation plate that can be fitted to a selected part of the lower jaw.

14. A jaw displacement system for treatment of sleep apnoea and/or snoring, comprising:

a first and a second bone anchor, wherein each bone anchor contains a fixation plate which is configured to attach the bone anchor to a bone of an upper or lower jaw, wherein this fixation plate is connected to a first rod that leads to a mount and wherein the first rod is configured to pass through gums when the bone anchor is attached to said bone, such that the mount is configured to be located in the oral cavity, wherein said first bone anchor is designed with said fixation plate that is intended to be fixed to a selected part of the upper jaw and said second bone anchor is designed with said fixation plate that is intended to be fixed to a selected part of the lower jaw, wherein the second bone anchor is configured to be positioned anterior to the first bone anchor, a jaw displacer having a first end and a second end, comprising a second rod disposed at the first end and a rod guide disposed at the second end, the second rod is movable in a longitudinal direction of the rod guide and detachable in relation to the rod guide by sliding the rod guide with respect to the second rod along the longitudinal direction, couplers allowing each of said ends of the jaw displacer to be detachably connected to the mount of the first or second bone anchor respectively, each of said couplers comprising a hook and eye, in which the hook can be attached in a detachable manner in the eye, wherein the eye is fixed with the rod guide and has a central axis that is parallel to the longitudinal direction of the rod guide, while the hook is provided on the mount of the respective bone anchor, wherein, when both bone anchors are configured to be attached to respective upper and lower jaws, the mount of the second bone anchor is positioned anterior and inferior to the mount of the first bone anchor and a connecting line is established between the couplers of said ends of the jaw displacer, said connecting line configured to extend on a side of the lower jaw inferior to a rotation point of the lower jaw in relation to the upper jaw when the upper and lower jaws are configured to be in a closed position, and wherein said rod guide contains a spring so that the rod guide can be deformed in its longitudinal direction between a compressed state and an extended state, and wherein the spring cooperates with said second rod, when the jaw displacement system is mounted in a user's oral cavity, to exert a pushing force on the second rod in the longitudinal direction of the rod guide so that the lower jaw is moved forward in an anterior direction in relation to the upper jaw.

15. The jaw displacement system according to claim 14, wherein the rod guide contains a tube with a first tube end and a second tube end, wherein one of said couplers is provided at the first tube end, while the spring extends along the tube in an uncompressed state up to at least the second tube end.

16. The jaw displacement system according to claim 15, wherein the spring is coaxial with said tube.

17. The jaw displacement system according to claim 15, wherein the tube extends at least partially in the spring.

18. The jaw displacement system according to claim 15, wherein said tube is a telescopic tube with parts which can freely move in relation to each other, said parts configured to be moved between a retracted position and an extended position, wherein said spring exerts a pushing force on said parts according to said longitudinal direction to bring said parts to said extended position.

19. The jaw displacement system according to claim 15, wherein opposite ends of said spring are connected with respectively said first and said second tube ends.

20. The jaw displacement system according to claim 15, wherein said second rod is provided with a ring or stop tube for said spring and/or said tube.

21. The jaw displacement system according to claim 14, wherein said rod guide contains a tube with a first tube end and a second tube end, one of said couplers is provided at the first tube end, while the spring connects to the second tube end and extends in prolongation of the tube.

22. The jaw displacement system according to claim 14, wherein the spring comprises a cylindrical coil spring.

23. The jaw displacement system according to 14, wherein one of said eyes is fixed to said second end.

24. A jaw displacement system for treatment of sleep apnoea and/or snoring, comprising:

a first and a second bone anchor, where each bone anchor contains a fixation plate configured to attach the bone anchor to a bone of an upper or lower jaw, where the fixation plate is connected to a connector that leads to a mount and where the connector is configured to pass through gums when the bone anchor is attached to said bone, such that the mount is configured to be located in the oral cavity, wherein said first bone anchor is designed with said fixation plate that is intended to be fixed to a selected part of the upper jaw and said second bone anchor is designed with said fixation plate that is intended to be fixed to a selected part of the lower jaw, wherein the second bone anchor is configured to be positioned anterior to the first bone anchor, a jaw displacer having a first end and second end, having a rod disposed at said first end and a rod guide disposed at said second end, the rod being movable in a longitudinal direction of the rod guide and detachable in relation to the rod guide, couplers allowing each of said ends of the jaw displacer, respectively, to be connected in a detachable manner to the mount of the first or second bone anchor, respectively, wherein, when both bone anchors are configured to be attached to the respective jaws, the mount of the second bone anchor is positioned anterior and inferior to the mount of the first bone anchor and a connecting line is established between the couplers of said ends of the jaw displacer, said connecting line configured to extend on a side of the lower jaw inferior to a rotation point of the lower jaw in relation to the upper jaw when the upper and lower jaws are configured to be in a closed position, and wherein each of said couplers comprise a hook and eye, where the hook can be attached to the eye in a detachable manner and wherein the eye is fixed with the rod guide and has a central axis perpendicular to a plane extending along the eye, wherein the central axis is parallel to the longitudinal direction of the rod guide, while the hook is provided on the mount of the respective bone anchor, wherein said rod guide contains a spring so that the rod guide can be deformed in its longitudinal direction between a compressed state and an extended state, and wherein the spring cooperates with said rod, when the jaw displacement system is mounted in the oral cavity, to exert a pushing force on the second rod in the longitudinal direction of the rod guide so that the lower jaw is moved forward in an anterior direction in relation to the upper jaw.

25. The jaw displacement system according to claim 24, where one of said eyes is fixed to said second end.

* * * * *